(12) United States Patent
Yoshida et al.

(10) Patent No.: US 12,209,242 B2
(45) Date of Patent: Jan. 28, 2025

(54) siRNA BASED ON RNA SEQUENCE OF SARS-CoV-2 AND USE THEREOF

(71) Applicants: TOAGOSEI CO., LTD., Tokyo (JP); KYOTO UNIVERSITY, Kyoto (JP)

(72) Inventors: Tetsuhiko Yoshida, Ibaraki-ken (JP); Nahoko Baileykobayashi, Ibaraki-ken (JP); Kazuo Takayama, Kyoto (JP); Rina Hashimoto, Kyoto (JP); Yoshinori Yoshida, Kyoto (JP)

(73) Assignees: TOAGOSEI CO., LTD., Tokyo (JP); KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 17/811,961

(22) Filed: Jul. 12, 2022

(65) Prior Publication Data

US 2023/0047473 A1    Feb. 16, 2023

(30) Foreign Application Priority Data

Jul. 14, 2021 (JP) .................. 2021-116560
Mar. 30, 2022 (JP) .................. 2022-057168

(51) Int. Cl.
*C12N 15/11* (2006.01)
*C12N 15/113* (2010.01)

(52) U.S. Cl.
CPC ...... *C12N 15/1131* (2013.01); *C12N 2310/11* (2013.01); *C12N 2310/14* (2013.01)

(58) Field of Classification Search
None
See application file for complete search history.

(56) References Cited

FOREIGN PATENT DOCUMENTS

| CN | 111139242 A | 5/2020 |
|---|---|---|
| CN | 111330003 A | 6/2020 |
| CN | 114250229 A | 3/2022 |
| KR | 102272800 B1 | 7/2021 |
| WO | 2021204216 A1 | 10/2021 |
| WO | 2021224918 A1 | 11/2021 |
| WO | 2021231827 A2 | 11/2021 |

OTHER PUBLICATIONS

Extended European Search Report, EP 22185020.9, dated Jun. 12, 2022.
Devi, GR, "siRNA-based approaches in cancer therapy" Cancer Gene Therapy, (2006) vol. 13, No. 9, pp. 819-829.
Robson, B. "Techniques assisting peptide vaccine and peptidomimetic design. Sidechain exposure in the SARS-CoV-2 spike glycoprotein" Computers in Biology and Medicine 128 (2021) 104124, 24 pages.
Vogel, Annette B. et al. "BNT162b vaccines protect rhesus macaques from SARS-CoV-2" Nature, vol. 592, No. 7853, Apr. 8, 2021, pp. 283-289.

*Primary Examiner* — Ekaterina Poliakova-Georgantas
(74) *Attorney, Agent, or Firm* — Edwin S. Flores; Daniel J. Chalker; Chalker Flores, LLP

(57) ABSTRACT

The present disclosure provides siRNA that suppresses proliferation of new coronaviruses (SARS-CoV-2). The siRNA disclosed herein includes: a sense strand; and an antisense strand. The sense strand includes a target sequence comprising 19 to 23 bases in which a base at a 5' terminal is guanine (G) or cytosine (C), and an overhang comprising 2 to 4 bases added to a 3' terminal side of the target sequence. The antisense strand includes a sequence complementary to the target sequence, and an overhang comprising 2 to 4 bases added to a 3' terminal side of the complementary sequence. Here, at least a part of the target sequence contains at least a part of a base sequence encoding a signal peptide region of a spike protein (S protein) of SARS-CoV-2.

3 Claims, 10 Drawing Sheets

Specification includes a Sequence Listing.

siRNA BASED ON RNA SEQUENCE OF SARS-CoV-2 AND USE THEREOF

CROSS-REFERENCE TO RELATED APPLICATIONS

Priority is claimed on Japanese Patent Application No. 2021-116560 filed on Jul. 14, 2021 and Japanese Patent Application No. 2022-57168 filed on Mar. 30, 2022, the entire contents of which are incorporated in the present specification as a whole by reference.

INCORPORATION-BY-REFERENCE OF MATERIALS FILED ON COMPACT DISC

The present application includes a Sequence Listing which has been submitted in XML format via EFS-Web and is hereby incorporated by reference in its entirety. Said XML copy, created on Jul. 8, 2022, is named KYOD1000 SL.txt and is103 kilo bytes in size.

BACKGROUND OF THE INVENTION

The present disclosure relates to siRNA that suppresses growth of a new coronavirus (severe acute respiratory syndrome coronavirus 2, SARS-CoV-2) and use thereof.

SARS-CoV-2 is a virus that infects humans and causes coronavirus disease 2019 (COVID-19) and is a pathogenic virus that rapidly causes symptoms such as severe pneumonia and sometimes kills infected persons. Since the discovery of an infectious disease due to this virus from December 2019 to early 2020, the infection has spread throughout the world and is a viral infectious disease that has a serious impact on the world economy and human life like SARS, MERS, or the like conventionally known.

A structure of a spike protein (hereinafter, also referred to as an "S protein") contributing to an infection route of SARS-CoV-2 is disclosed in Computers in Biology and Medicine, Vol. 128, 2021, Article Number 104124. S proteins of SARS-CoV-2 are present on the surface of virus particles and bind to angiotensin conversion enzyme II (ACE2) present on cell membranes of human cells to promote invasion of the virus particles into human cells.

SUMMARY OF THE INVENTION

Incidentally, various mutant strains in which S protein of SARS-CoV-2 has mutated have been reported with the spread of infection with SARS-CoV-2. Mutations of the S protein may cause problems such as an increase in binding force of human cells to ACE2, an increase in infectivity, and a change in structures of the S protein, which are difficult for existing antibodies to recognize. For this reason, in order to suppress the spread of infection with SARS-CoV-2, not only an approach from immunochemistry such as development of antibody drugs or vaccines that promote production of antibodies but also an approach from various aspects is required.

Therefore, the present disclosure has been made from the viewpoint of the circumstances, and a main purpose of the present disclosure is to provide siRNA that suppresses proliferation of SARS-CoV-2. In addition, as another aspect, another purpose thereof is to provide a composition containing the siRNA. In addition, still another purpose thereof is to provide a method of using the composition.

The present inventors have conjectured that the proliferation of SARS-CoV-2 can be suppressed by suppressing expression(s) of specific protein(s) of SARS-CoV-2 due to RNA interference (RNAi). Here, the present inventors have focused on a signal peptide region as a target sequence of RNAi. Since the signal peptide region is a part that instructs transportation and localization of proteins, it can be stated that the signal peptide region is one of indispensable regions for proteins to appropriately exhibit their inherent functions. For this reason, it is inferred that SARS-CoV-2 in which a signal peptide region had mutated would not be able to appropriately maintain original functions of proteins and would be likely to be culled. Accordingly, in SARS-CoV-2 (including mutant strains) with widespread infection, it is inferred that a signal peptide region is unlikely to mutate and the sequence would tend to be conserved. That is, it is inferred that, if an effect of suppressing proliferation of SARS-CoV-2 due to RNAi targeting a signal peptide region can be obtained, an effect of suppressing proliferation of various kinds of SARS-CoV-2 which include mutant strains and may spread can also be obtained.

Therefore, the present inventors have conducted extensive studies, and as a result, have found that the proliferation of SARS-CoV-2 can be significantly suppressed using siRNA having a base sequence containing at least a part of a base sequence encoding a signal peptide region of the S protein of SARS-CoV-2. On the other hand, surprisingly, in siRNA targeting at least a part of a base sequence encoding a signal peptide region of an ORF8 protein possessed by SARS-CoV-2, there is no effect of suppressing proliferation of SARS-CoV-2 observed (the details will be shown in test examples to be described below). That is, it has been found that the effect of suppressing proliferation of SARS-CoV-2 is not obtained by siRNA simply targeting a signal peptide region, but is obtained by siRNA targeting a signal peptide region of the S protein.

The siRNA disclosed herein includes a sense strand and an antisense strand. The sense strand includes a target sequence comprising 19 to 23 bases in which a base at a 5' terminal is guanine (G) or cytosine (C), and an overhang comprising 2 to 4 bases added to a 3' terminal side of the target sequence. The antisense strand includes a sequence complementary to the target sequence, and an overhang comprising 2 to 4 bases added to a 3' terminal side of the complementary sequence. Moreover, at least a part of the target sequence contains at least a part of a base sequence encoding a signal peptide region of a spike protein (S protein) of SARS-CoV-2.

The siRNA having such a configuration can suppress the expression level of the S protein and suppress proliferation of SARS-CoV-2.

In addition, in a preferred aspect of the siRNA disclosed herein, at least 3 bases out of 5 bases on the 3' terminal side of the target sequence are adenine (A) or uracil (U). This facilitates incorporation of an antisense strand into an RNA-induced silencing complex (RISC) which is a protein involved in RNAi, and therefore, RNAi is more suitably induced and the effect of suppressing proliferation of SARS-CoV-2 is more efficiently exhibited.

In addition, in a preferred aspect of the siRNA disclosed herein, the target sequence includes any one of (1) to (7) below:

(1)
(SEQ ID NO: 1)
GUUUAUUGCCACUAGUCU;

(2)
(SEQ ID NO: 2)
GUCUCUAGUCAGUGUGUUA;

(3)
(SEQ ID NO: 3)
CAGUGUGUUAAUCUUACAA;

(4)
(SEQ ID NO: 31)
GUUUGUUUUCUUGUUUUA;

(5)
(SEQ ID NO: 32)
CCACUAGUCUCUAGUCAGU;

(6)
(SEQ ID NO: 33)
CUCUAGUCAGUGUGUUAAU;
and (7)
(SEQ ID NO: 34)
CUAGUCAGUGUGUUAAUCU.

Since the sequences shown in (1) to (7) above contain at least a part of a base sequence encoding a signal peptide region of the S protein, expression of the S protein can be suitably suppressed and the proliferation of SARS-CoV-2 can be effectively suppressed.

In addition, in a preferred aspect of the siRNA disclosed herein, base sequences constituting the overhangs are thymine-thymine (TT). Accordingly, RNAi can be easily induced.

In addition, in order to realize the purposes, the present disclosure provides a composition used for suppressing proliferation of SARS-CoV-2. The composition disclosed herein contains the siRNA disclosed herein. In addition, the present disclosure provides a method for treating infection with SARS-CoV-2. One aspect of the treatment method disclosed herein includes administration of the composition disclosed herein to animals. Accordingly, the proliferation of SARS-CoV-2 in animal individuals infected with SARS-CoV-2 can be suppressed, and symptoms caused by the infection with SARS-CoV-2 can be alleviated.

DETAILED DESCRIPTION OF THE INVENTION

Figure 1:
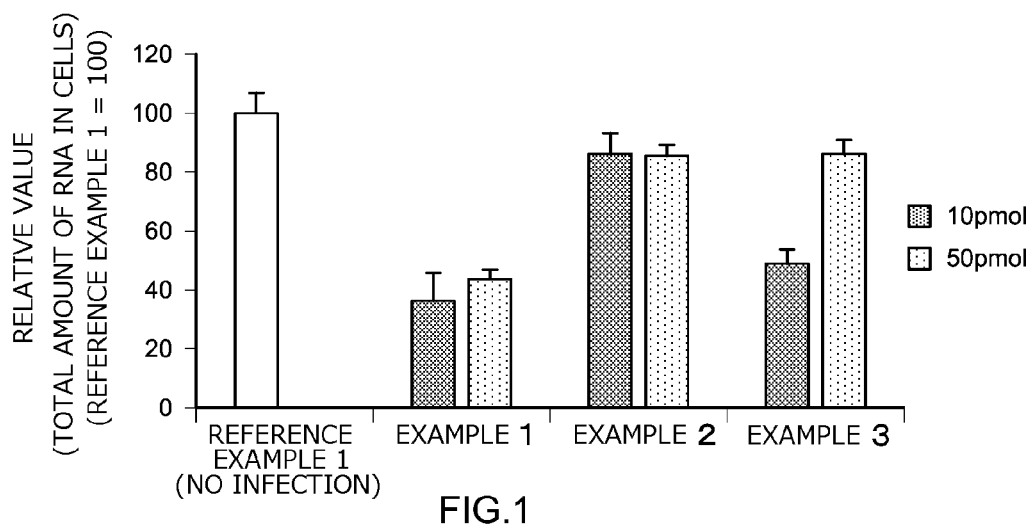
FIG. 1 is a graph showing a total amount of RNA obtained from cells after infection with SARS-CoV-2 and transfection with siRNA shown in Examples 1 to 3.

Hereinafter, technology disclosed herein will be described in detail. Matters (for example, general matters relating to synthesis methods of polynucleotides and the like) other than those (for example, configurations of siRNA) specifically mentioned in the present specification and necessary for the implementation of the present technology can be understood by those skilled in the art as design matters based on the conventional art in the fields such as cell engineering, physiology, medicine, pharmacy, organic chemistry, biochemistry, genetic engineering, protein engineering, molecular biology, and genetics. The technology disclosed herein can be implemented based on the contents disclosed in the present specification and common technical knowledge in the field.

The term "polynucleotide" in the present specification refers to a polymer in which a plurality of (two or more) nucleotides are bound through a phosphoric diester bond, and the number of nucleotides is not limited. For example, one containing a deoxyribonucleotide and a ribonucleotide as nucleotides is also included in the "polynucleotide" in the present specification.

In addition, an "artificially designed polynucleotide" in the present specification refers to a polynucleotide of which nucleotide chains (full length) are not present in nature on their own and which is artificially synthesized through chemical synthesis or biosynthesis (that is, production based on genetic engineering).

In addition, in the present specification, the left side of a base sequence always indicates a 5' terminal side and the right side thereof always indicates a 3' terminal side unless notation of "5'" and "3'" is added.

In addition, in the present specification, a numerical range described as A to B (here, A and B are arbitrary numbers) is the same as the generally interpreted range and means A or more and B or less (including a range more than A and less than B).

The siRNA disclosed herein includes: a sense strand; and an antisense strand. In addition, the siRNA disclosed herein may be composed of the sense strand and the antisense strand. The sense strand includes a target sequence having the same base sequence as a part of a base sequence of genomic RNA of SARS-CoV-2, and the antisense strand includes a sequence complementary to the target sequence of the sense strand. The sense strand and the antisense strand are hybridized at a target sequence portion, and siRNA forms a double strand. The sense strand and the antisense strand are artificially synthesized polynucleotides.

SARS-CoV-2 is known to be a single-stranded RNA virus, and a sequence of genomic RNA thereof is available from, for example, a database of the National Center for Biotechnology Information (NCBI). Depending on databases, a genome sequence of SARS-CoV-2 is written as thymine (T) instead of uracil (U). In this case, T can be replaced with U by considering that SARS-CoV-2 is a single-stranded RNA virus.

RNAi can be induced through introduction of siRNA into cells. Typically, but not necessarily limited to this mechanism, after siRNA is introduced into cells, an antisense strand is incorporated into an RNA-induced silencing complex (RISC). Then, RNA having a sequence complementary to a sequence (that is, a target sequence) contained in the antisense strand is recognized and is cleaved or inhibited from being translated. Accordingly, it is possible to suppress expression of a desired protein. With such a mechanism, the siRNA disclosed herein suppresses expression of S proteins of SARS-CoV-2 to suppress proliferation of SARS-CoV-2.

The target sequence disclosed herein includes the same base sequence as a part of genomic RNA of SARS-CoV-2. In addition, the target sequence contains at least a part of a base sequence (hereinafter, also referred to as an "SP base sequence") encoding a signal peptide region of an S protein of SARS-CoV-2.

In the present specification, a "signal peptide region of an S protein" refers to a peptide region comprising an amino acid sequence (SEQ ID NO: 4) from the 1st to 16th positions of an S protein of SARS-CoV-2 as disclosed in Computers in Biology and Medicine, Vol. 128, 2021, Article Number 104124 and Nature, Vol. 592, No. 7853, 2021, pp. 283-289. That is, a "base sequence (SP sequence) encoding a signal peptide region of an S protein" in the present specification refers to a base sequence consisting of 48 bases shown in SEQ ID NO: 5.

The proportion of a sequence contained in an SP base sequence in a target sequence is, for example, preferably 45% or more when the entire target sequence is set to 100%, and may be 60% or more, 75% or more, 90% or more, or 100%. Since it is inferred that a base sequence encoding a signal peptide region is a sequence unlikely to mutate, a target sequence having such a proportion can exhibit a proliferation-suppressing effect also on various SARS-CoV-2 mutant strains which can spread.

In a case where the target sequence contains a base sequence other than a sequence derived from the SP base sequence, the base sequence other than the sequence derived from the SP base sequence is provided on the 5' terminal side or the 3' terminal side of the sequence derived from the SP base sequence. That is, the target sequence may contain a base sequence continuous on the 5' terminal side of the SP base sequence of genomic RNA of SARS-CoV-2 or may contain a base sequence continuous on the 3' terminal side of the SP base sequence. These sequences can be confirmed, for example, in the database published by the NCBI.

The length of the target sequence may be the same as that designed for siRNA conventionally known. For example, it may be 19 bases or more and 23 bases or less, or 19 bases or more and 21 bases or less, or may be 19 bases. Accordingly, RNAi can be suitably induced in cells, and proliferation of SARS-CoV-2 can be suppressed.

The target sequence is typically composed of polynucleotides which are polymers of ribonucleotides. In other words, the target sequence is composed of RNA. That is, a base sequence of the target sequence is typically represented by the four letters of A (adenine), U (uracil), G (guanine), and C (cytosine) or the four letters of a, u, g, and c.

The 5' terminal of the target sequence is preferably guanine or cytosine. Since guanine and cytosine have a higher binding force to complementary strands than adenine and uracil, the stability on the 5' terminal side of a sense strand (that is, on the 3' terminal side of an antisense strand) is improved. In other words, the stability on the 5' terminal side of the antisense strand becomes relatively low. Although the details of the mechanism are not clear, the RISC tends to preferentially incorporate a chain of which the 5' terminal side is more energetically unstable between the sense strand and the antisense strand. For this reason, when the 5' terminal of the target sequence is guanine or cytosine, the antisense strand is easily incorporated into the RISC, and RNAi can be more suitably induced. As a result, an effect of suppressing proliferation of SARS-CoV-2 is more suitably exhibited.

60% or more (that is, 3 bases or more) of 5 bases on the 3' terminal side of the target sequence are preferably adenine and uracil, and 80% or more (that is, 4 bases or more) thereof may be adenine and uracil or 100% (that is, 5 bases) thereof may be adenine and uracil. Accordingly, the stability on the 5' terminal side of the antisense strand becomes relatively lower than that on the 3' terminal side. As a result, the antisense strand can be easily incorporated into the RISC, and RNAi can be more suitably induced. As a result, an effect of suppressing proliferation of SARS-CoV-2 is more suitably exhibited.

The GC content (the total proportion G and C in an entire base sequence constituting a target sequence) of the entire target sequence is not particularly limited, but may be, for example, 20% or more and 60% or less, preferably 30% or more and 50% or less, or may be 30% or more and 45% or less. The GC content can be a parameter relating to, for example, ease of cleavage of RNA or a binding force between RNA having a target sequence and an antisense strand incorporated into the RISC. With the GC content, the effect of RNAi can be suitability exhibited.

The sense strand preferably has an overhang in addition to the target sequence. The overhang is a base sequence added to the 5' terminal side or the 3' terminal side of the target sequence. The overhang is preferably added to the 3' terminal side of the target sequence. When the overhang is added, RNAi is more effectively induced. Therefore, proliferation of SARS-CoV-2 can be suitably suppressed.

The overhang is composed of a base sequence comprising 2 to 4 bases and preferably composed of a base sequence consisting of 2 bases. A base sequence constituting an overhang is not particularly limited, and suitable examples thereof include thymine-thymine (TT) and uracil-uracil (UU). In a case where an overhang is TT, the overhang is composed of DNA.

An overhang is composed of polynucleotides (dimers, trimers, or tetramers). Polynucleotides constituting an overhang may be composed of only ribonucleotides, only deoxynucleotides, or both deoxynucleotides and ribonucleotides. That is, an entirety of a sense strand and an antisense strand may be RNA or may be chimeric polynucleotides of RNA and DNA. In addition, an overhang may contain modified deoxyribonucleotides, modified ribonucleotides, other well-known nucleotide analogs, and the like.

A sense strand is composed of, for example, a base sequence with 21 bases or more and 27 bases or less, and may be composed 21 bases or more and 25 bases or less, or 21 bases or more and 23 bases or less. In one suitable example, a sense strand is composed of 21 bases including 19 bases of a target sequence and 2 bases of an overhang. In the example, RNAi is effectively induced. Therefore, proliferation of SARS-CoV-2 can be suitably suppressed.

An antisense strand has a base sequence complementary to a target sequence of a sense strand. Accordingly, the antisense strand is hybridized with the sense strand to form a double-stranded structure. The portion of the complementary base sequence is typically composed of a polymer of ribonucleotides (RNA).

The antisense strand has an overhang similarly to the sense strand. The overhang is added to the 5' terminal side or the 3' terminal side of the complementary base sequence. In one preferred example, when an overhang of a sense strand is added to the 3' terminal side of the target sequence, an overhang of an antisense strand is added to the 3' terminal side of the complementary base sequence.

The configuration of the overhang of the antisense strand may be the same as that of the overhang of the sense strand. Typically, the base sequence of the overhang of the antisense strand is the same as that of the overhang of the sense strand to be hybridized, but may be a base sequence different therefrom.

An antisense strand is composed of, for example, a base sequence with 21 bases or more and 27 bases or less, and may be composed 21 bases or more and 25 bases or less, or 21 bases or more and 23 bases or less. In one suitable example, an antisense strand is composed of a base sequence having the same length as a sense strand, and the entire base sequence excluding overhangs is complementary to a target sequence of the sense strand.

Specific examples of suitable sequences as target sequences of the siRNA disclosed herein include the following base sequences represented by SEQ ID NOS: 1 to 3 and 31 to 34:

(1)
(SEQ ID NO: 1)
GUUUUAUUGCCACUAGUCU;

(2)
(SEQ ID NO: 2)
GUCUCUAGUCAGUGUGUUA;

(3)
(SEQ ID NO: 3)
CAGUGUGUUAAUCUUACAA;

(4)
(SEQ ID NO: 31)
GUUUGUUUUCUUGUUUUA;

(5)
(SEQ ID NO: 32)
CCACUAGUCUCUAGUCAGU;

-continued (6)
(SEQ ID NO: 33)
CUCUAGUCAGUGUGUUAAU;
and (7)
(SEQ ID NO: 34)
CUAGUCAGUGUGUUAAUCU.

The base sequences represented by SEQ ID NOS: 1 to 3 and 31 to 34 are all composed of RNA.

The base sequence represented by SEQ ID No: 1 is a base sequence from the 16th to 34th positions of a base sequence encoding an S protein of SARS-CoV-2 and is a partial base sequence of the SP base sequence.

The base sequence represented by SEQ ID No: 2 is a base sequence from the 31st to 49th positions of a base sequence encoding an S protein of SARS-CoV-2. Of the base sequence shown in SEQ ID NO: 2, the base sequence from the 1st to 18th positions is a part of the SP base sequence, and A at the 19th position is a sequence outside the SP base sequence.

The base sequence represented by SEQ ID No: 3 is a base sequence from the 40th to 58th positions of a base sequence encoding an S protein of SARS-CoV-2. Of the base sequence shown in SEQ ID NO: 3, the base sequence from the 1st to 9th positions is a part of the SP base sequence, and the base sequence from the 10th to 19th positions is a sequence outside the SP base sequence.

The base sequence represented by SEQ ID No: 31 is a base sequence from the 3rd to 21st positions of a base sequence encoding an S protein of SARS-CoV-2 and is a partial base sequence of the SP base sequence.

The base sequence represented by SEQ ID No: 32 is a base sequence from the 25th to 43rd positions of a base sequence encoding an S protein of SARS-CoV-2 and is a partial base sequence of the SP base sequence.

The base sequence represented by SEQ ID No: 33 is a base sequence from the 33rd to 51st positions of a base sequence encoding an S protein of SARS-CoV-2. Of the base sequence shown in SEQ ID NO: 33, the base sequence from the 1st to 16th positions is a part of the SP base sequence, and the base sequence from the 17th to 19th positions is a sequence outside the SP base sequence.

The base sequence represented by SEQ ID No: 34 is a base sequence from the 35th to 53rd positions of a base sequence encoding an S protein of SARS-CoV-2. Of the base sequence shown in SEQ ID NO: 34, the base sequence from the 1st to 14th positions is a part of the SP base sequence, and the base sequence from the 15th to 19th positions is a sequence outside the SP base sequence.

siRNA in which a target sequence is composed of any of SEQ ID NOS: 1 to 3 and 31 to 34 can significantly suppress proliferation of SARS-CoV-2 as shown in test examples to be described below.

A sense strand and an antisense strand constituting the siRNA disclosed herein can be produced according to a general chemical synthesis method. For example, these can be synthesized using a commercially available DNA/RNA automatic synthesizer. In addition, siRNA may be synthesized in vitro or in vivo based on a genetic engineering technique. The synthesized sense strand and antisense strand are preferably purified and can be purified using, for example, HPLC.

The siRNA disclosed herein can be produced by, for example, annealing (hybridizing) a sense strand and an antisense strand. The annealing method may follow a well-known conventional method, and the annealing temperature, the cooling rate, and the like may be adjusted depending on a base sequence constituting a target sequence. For example, annealing can be performed by mixing a sense strand and an antisense strand in equal amounts in a solvent, heating the mixture at 90° C. for 1 to 5 minutes, and cooling the heated mixture to 4° C. to room temperature. For example, distilled water, pure water, ultrapure water, a buffer (for example, a 30 mM to 50 mM HEPES-KOH buffer at pH 7.4), and the like can be used as a solvent. In order to prevent active RNase (RNA-degrading enzyme) from being mixed in the solvent, a solvent that has been subjected to, for example, a DEPC treatment, an autoclave treatment, and the like is preferably used.

siRNA may be in the form of a solution obtained by dissolving siRNA in a solvent, or in the form of gel or powder.

Although the siRNA disclosed herein has been described, the present disclosure further provides a composition containing the siRNA disclosed herein. The composition disclosed herein may be provided as a composition which may contain various carriers pharmaceutically acceptable depending on use forms. Regarding carriers, for example, carriers commonly used as diluents, excipients, and the like in pharmaceuticals are preferable. Although the carriers may appropriately vary depending on the applications or forms of the composition, typical examples thereof include water, a physiological buffer solution, and various organic solvents. In addition, such a carrier may be an aqueous alcohol (such as ethanol) solution at an appropriate concentration, glycerol, and non-drying oils such as olive oil, or may be a liposome. In addition, examples of secondary components that can be contained in the pharmaceutical composition include various fillers, extenders, binders, humectants, surfactants, pigments, and fragrances. In addition, carriers used in drug delivery systems conventionally known may be included.

The form of the composition is not particularly limited. Examples of typical forms thereof include a liquid medicine, suspensions, emulsions, aerosols, foaming agents, granules, powdery agents, tablets, capsules, and ointments. In addition, the forms thereof may be freeze-dried products or granulated products for preparing a drug solution by dissolving the composition in physiological saline or a suitable buffer solution (for example, PBS) immediately before use in order to use the composition for injection or the like.

Since the process itself for preparing various forms of medicines (compositions) using siRNA (main component) and various carriers (secondary components) as materials may be based on a well-known conventional method and such a method itself for preparing a formulation does not characterize the present disclosure, detailed description thereof will be omitted. Examples of detailed information sources on prescription include Comprehensive Medicinal Chemistry, supervised by Corwin Hansch, published by Pergamon Press (1990).

In addition, the composition may contain the siRNA disclosed herein alone or in combination of two or more thereof. By incorporating two or more kinds of siRNA, the number of sequence species targeted for suppressing expression increases, and therefore suppression of proliferation of SARS-CoV-2 can be more suitably realized. On the other hand, in a case where siRNA is contained alone, the risk (a so-called off-target effect) of inhibiting translation of mRNA of a host cell having a base sequence similar to a target sequence is reduced. Since the siRNA disclosed herein can significantly suppress proliferation of SARS-CoV-2 even when used alone, it can be suitably used even when used alone.

In addition, the present disclosure provides a method for treating infection with SARS-CoV-2 using the composition disclosed herein. The treatment method disclosed herein includes administration of the composition disclosed herein in humans or animals except humans. SARS-CoV-2 is a virus that can infect not only humans but also non-human animals. Examples of such animals include mammals such as dogs, cats, tigers, lions, ferrets, minks, hamsters, and monkeys.

The method for administering a composition is not particularly limited as long as it is according to conventional methods used for treating animals. The composition can be used in vivo in a method or a dose depending on the form or purpose thereof. For example, the composition can be administered as a liquid agent to a lesion part (for example, malignant tumor tissue, virus-infected tissue, and inflamed tissue) of a patient or an animal individual (that is, a living body) in a desired amount through intravenous, intramuscular, subcutaneous, intradermal, or intraperitoneal injection. Alternatively, the composition in a solid form such as a tablet, or a gel form or an aqueous jelly form such as an ointment can be directly administered to a predetermined tissue (that is a lesion part such as an organ or tissue containing, for example, tumor cells, virus-infected cells, and inflamed cells). Alternatively, the composition in a solid form such as a tablet can be orally administered. In the case of oral administration, it is preferable to apply encapsulation or a protective (coating) material to suppress digestive enzyme decomposition in the digestive tract.

In addition, the siRNA and the composition disclosed herein can also be used for eukaryotic cells in vitro. Examples of eukaryotic cells in vitro include various kinds of cell aggregations, tissues, organs, blood, lymph, and cell lines removed from a living body. When these are used in vitro, siRNA can be mixed, for example, with various commercially available transfection reagents. The concentration of siRNA is not particularly limited, but can be, for example, 1 nM or more or 5 nM or more (for example, 6.25 nM or more) in a culture medium of eukaryotic cells. In addition, from the viewpoint of transfection efficiency, the concentration of siRNA may be, for example, 1 µM or less, and may be 100 nM or less, 50 nM or less, 25 nM or less, and 12.5 nM or less. Furthermore, since the siRNA disclosed herein exhibits a significant effect of suppressing SARS-CoV-2 even at a low concentration, the concentration of the siRNA may be, for example, 10 nM or less, 8 nM or less, or 6.5 nM or less.

In addition, the target sequence contained in the siRNA disclosed herein can also be used for short hairpin RNA (shRNA). shRNA is RNA in which a target sequence and a sequence complementary to the target sequence are present on a single strand, and a loop sequence for forming a loop structure is present therebetween. Since shRNA has a loop structure, the target sequence and the complementary sequence thereof are hybridized to form a local double-stranded structure. Accordingly, shRNA is processed by Dicer which is an enzyme present in a cell, and the siRNA disclosed herein can be formed.

The configuration of shRNA may be the same as that of the conventionally known shRNA. The length of shRNA may be, for example, 50 to 70 bases. In addition, the length of a loop sequence may be, for example, 19 to 29 bases. In addition, a vector (for example, a lentivirus expression vector) may be integrated with shRNA. By using shRNA, RNAi can be stably induced in cells, and therefore, proliferation of SARS-CoV-2 can be stably suppressed.

Hereinafter, some test examples relating to the technology disclosed herein will be described. However, the technology disclosed herein is not limited to those shown in the test examples.

Preparation of siRNA

Eurofins Genomics K.K. was asked to synthesize polynucleotides, and 12 kinds of polynucleotides were obtained. Base sequences of the polynucleotides are shown in Table 1. In each polynucleotide, "TT" (overhang) on the 3' terminal side is DNA, and the other portion of the sequence (target sequence) is composed of RNA. The obtained polynucleotides were used to prepare siRNAs used in Examples 1 to 6 by annealing sense strands and antisense strands having complementary sequences.

TABLE 1

Configuration of siRNA

| Example 1 | Sense strand: | 5' | GUUUUAUUGCCACUAGUCUTT | 3' | (SEQ ID NO: 6) |
|---|---|---|---|---|---|
|  | Antisense strand: | 3' | TTCAAAAUAACGGUGAUCAGA | 5' | (SEQ ID NO: 7) |
| Example 2 | Sense strand: | 5' | GUCUCUAGUCAGUGUGUUATT | 3' | (SEQ ID NO: 8) |
|  | Antisense strand: | 3' | TTCAGAGAUCAGUCACACAAU | 5' | (SEQ ID NO: 9) |
| Example 3 | Sense strand: | 5' | CAGUGUGUUAAUCUUACAATT | 3' | (SEQ ID NO: 10) |
|  | Antisense strand: | 3' | TTGUCACACAAUUAGAAUGUU | 5' | (SEQ ID NO: 11) |
| Example 4 | Sense strand: | 5' | GUUUUCUUAGGAAUCAUCATT | 3' | (SEQ ID NO: 12) |
|  | Antisense strand: | 3' | TTCAAAAGAAUCCUUAGUAGU | 5' | (SEQ ID NO: 13) |
| Example 5 | Sense strand: | 5' | GCUGCAUUUCACCAAGAAUTT | 3' | (SEQ ID NO: 14) |
|  | Antisense strand: | 3' | TTCGACGUAAAGUGGUUCUUA | 5' | (SEQ ID NO: 15) |
| Example 6 | Sense strand: | 5' | CAAGAAUGUAGUUUACAGUTT | 3' | (SEQ ID NO: 16) |
|  | Antisense strand: | 3' | TTGUUCUUACAUCAAAUGUCA | 5' | (SEQ ID NO: 17) |

Examples 1 to 3 shown in Table 1 are siRNAs designed to contain at least a part of a base sequence encoding a signal peptide region of an S protein of the SARS-CoV-2. On the other hand, Examples 4 to 6 are siRNAs for ORF8 protein of SARS-CoV-2. The ORF8 protein has a signal peptide region. A sequence (SEQ ID NO: 18) from the 1st to 45th positions of a base sequence encoding the ORF8 protein is the base sequence encoding the signal peptide region.

The siRNA of Example 4 targets a base sequence from 13th to 31st positions (the sequence portion excluding TT of the sense strand of Example 4) of the base sequence encoding the ORF8 protein. That is, the siRNA of Example 4 is designed to be similar to a part in the base sequence encoding the signal peptide region of the ORF8 protein.

The siRNA of Example 5 targets a base sequence from 40th to 58th positions (the sequence portion excluding TT of the sense strand of Example 5) of the base sequence encoding the ORF8 protein. That is, the siRNA of Example 5 is designed to contain at least a part of the base sequence encoding the signal peptide region of the ORF8 protein.

The siRNA of Example 6 targets a base sequence from 52nd to 70th positions (the sequence portion excluding TT of the sense strand of Example 6) of the base sequence encoding the ORF8 protein. That is, the siRNA of Example 6 is designed not to contain the base sequence encoding the signal peptide region of the ORF8 protein.

Test 1
Introduction of siRNA into Cells and Viral Infection

Examples 1 to 6

In Test 1, effects of suppressing proliferation of SARS-CoV-2 of the above-prepared siRNAs were examined. For this examination, Huh7-ACE2 cells which were human liver cancer-derived cell strains transformed to stably express human ACE2 gene were used. In addition, Dulbecco's minimal essential medium (DMEM) containing 10% fetal bovine serum (FBS) was used as a culture medium for the Huh7-ACE2 cells. First, the Huh7-ACE2 cells were seeded in a 48-well plate for cell culture to have a density of $5 \times 10^4$ cells/well and cultured for 24 hours in an environment of 37° C. and 5% $CO_2$. Next, each of the above-prepared siRNAs was added to a well to have a concentration of 10 pmol/well (the siRNA concentration of 10 nM in the medium in the well) or 50 pmol/well (the siRNA concentration of 50 nM in the medium in the well) using Lipofectamine (trademark) RNAiMAX (manufactured by Thermo Fisher Scientific Inc.) which was a transfection reagent. Then, after the siRNA was cultured in an environment of 37° C. and 5% $CO_2$ for 6 hours, wild strains of SARS-CoV-2 were added to the well at $2 \times 10^4$ TCID50/well and further cultured for 2 hours. Thereafter, the well was washed with PBS, the culture medium was added to the well to further perform culture for 2 days, and then, the medium (supernatant) in the well was collected. Next, the collected supernatant was mixed with an equal amount of a 2×RNA lysis buffer (0.4 μL SUPERaseI (trademark) RNase Inhibitor (manufactured by Thermo Fisher Scientific Inc.), 2% TritonX-100, 50 mM KCl, 100 mM Tris-HCl (pH 7.4), and 40% glycerol), and the mixture was allowed to stand at room temperature for 10 minutes. Thereafter, the resultant was diluted 10 times with distilled water to prepare a supernatant sample for qPCR.

On the other hand, the cells in the well were collected, and RNA was isolated and collected using ISOGEN (purchased from NIPPON GENE CO., LTD.). The amount of RNA obtained through collection was measured based on the absorbance at 260 nm. Of the collected RNA, 500 ng of RNA was used to prepare cDNA (hereinafter, also referred to as a "cell extraction sample") using Superscript VILO cDNA Synthesis Kit (manufactured by Thermo Fisher Scientific Inc.).

Reference Example 1

In Reference Example 1, a supernatant sample and a cell extraction sample were obtained in the same manner as in Examples 1 to 6 described above except that transfection and addition of SARS-CoV-2 were not performed. That is, Reference Example 1 shows an example without infection with SARS-CoV-2.

Figure 2:
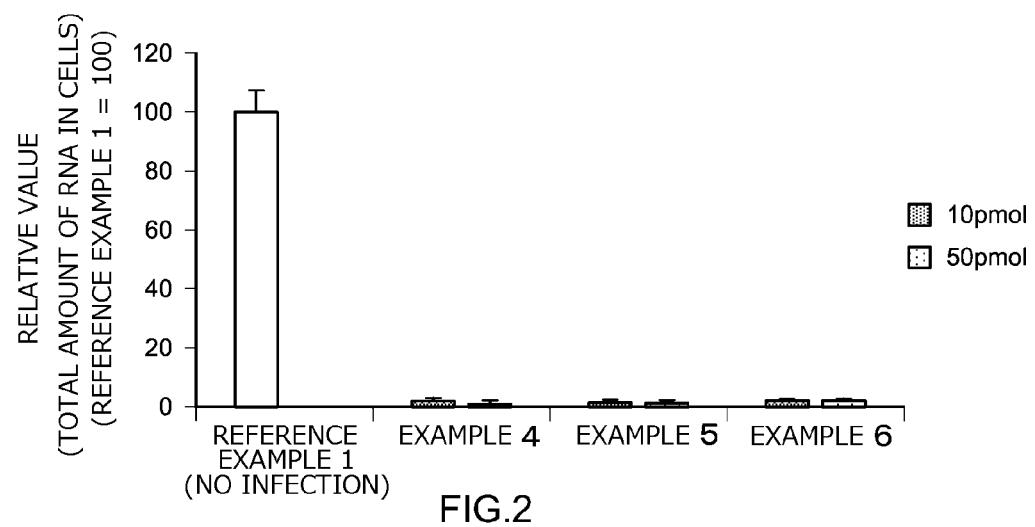
FIG. 2 is a graph showing a total amount of RNA obtained from cells after infection with SARS-CoV-2 and transfection with siRNA targeting a signal peptide region of ORF8 or its vicinity.

The total amounts of RNA obtained from the cells of the examples were compared with each other. In FIGS. 1 and 2, values when Reference Example 1 was set to 100% are shown, and it can be estimated that the lower the values, the lower the number of living cells.

As shown in FIG. 1, Examples 1 to 3 in which the siRNAs targeting at least a part of the base sequence encoding a signal peptide region of an S protein are transfected showed values 30% or more of those of Reference Example 1. In particular, Example 2 showed a value of about 80% thereof regardless the amount of siRNA added, and Example 3 showed a value of about 80% when 50 pmol of siRNA was added (the siRNA concentration of 50 nM). On the other hand, as shown in FIG. 2, Examples 4 to 6 targeting a signal peptide region of an ORF8 protein or its vicinity showed low values of 2% or less. From these results, it can be seen that, in a case where siRNA targeting at least a part of the base sequence encoding a signal peptide region of an S protein is transfected, RNA can be collected from cells infected with SARS-CoV-2.

Figure 3:
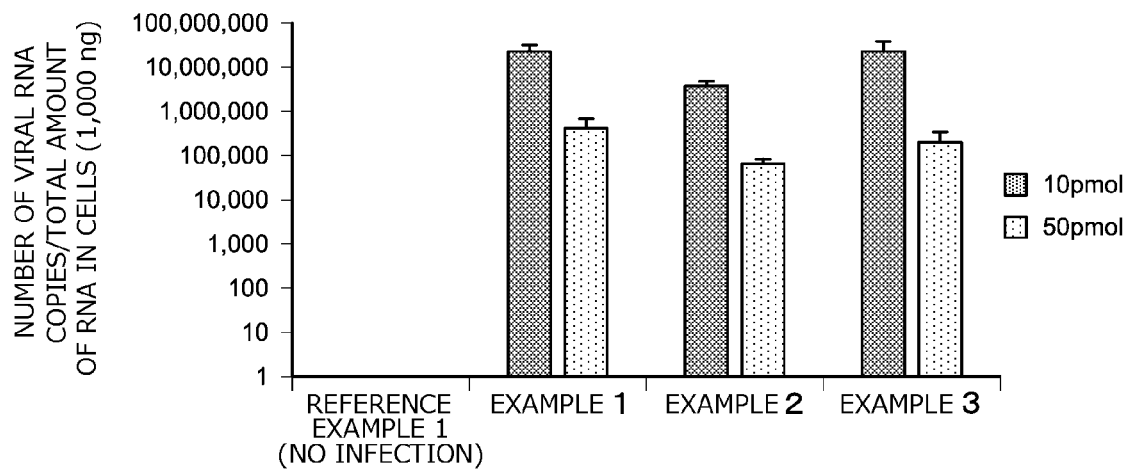
FIG. 3 is a graph showing the number of RNA copies of SARS-CoV-2 contained in a culture medium (supernatant sample) after infection with SARS-CoV-2 and transfection with siRNA shown in Examples 1 to 3, and the number of viral RNA copies is corrected by the total amount of RNA obtained from the cells.
Figure 4:
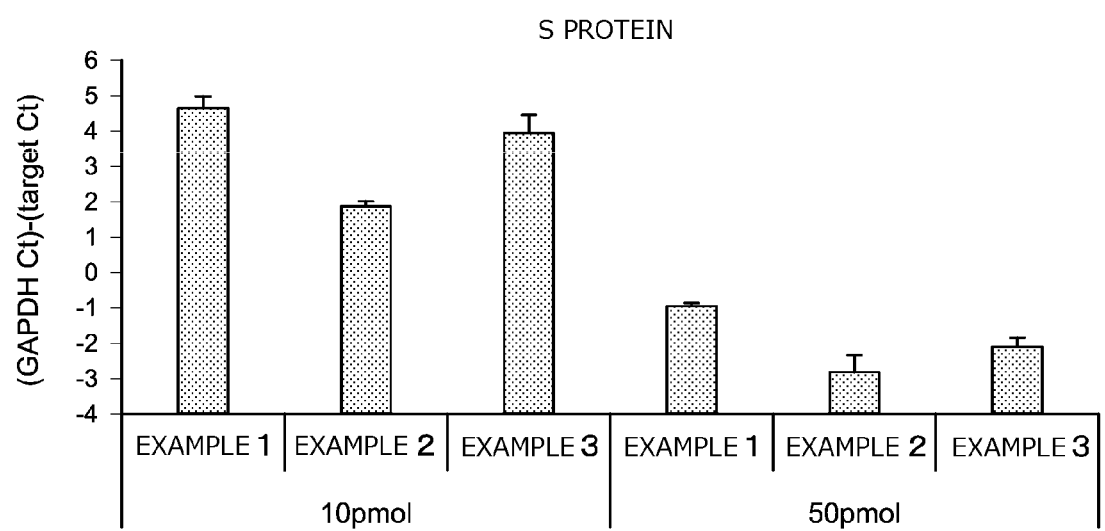
FIG. 4 is a graph showing changes in the amount of RNA of S protein contained in SARS-CoV-2-infected cell-extracted samples through transfection with siRNA shown in Examples 1 to 3.
Figure 5:
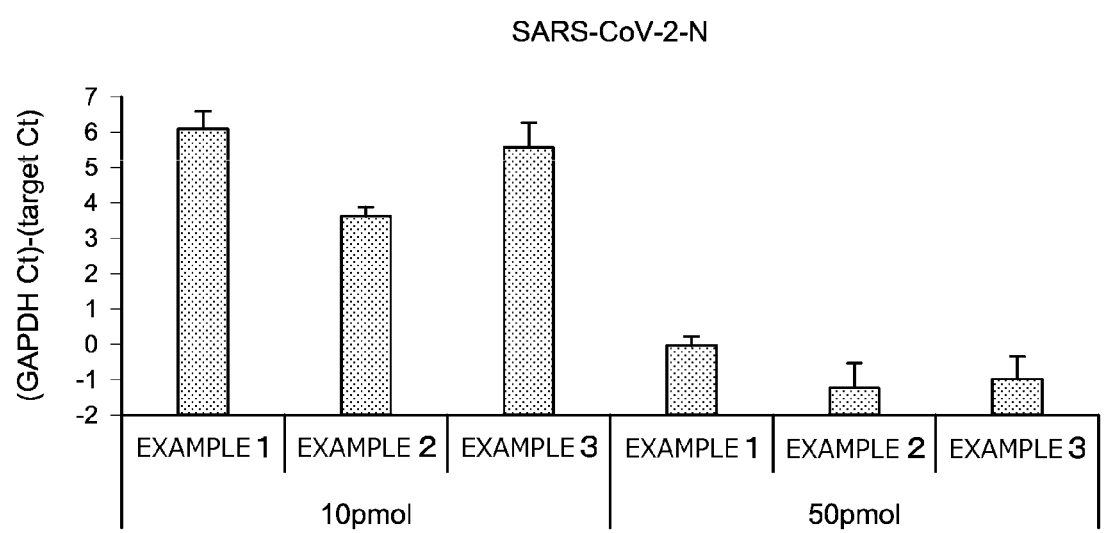
FIG. 5 is a graph showing changes in the amount of RNA of nucleocapsid protein (hereinafter, also referred to as "N protein") in SARS-CoV-2 contained in SARS-CoV-2-infected cell-extracted samples through transfection with siRNA shown in Examples 1 to 3.
Figure 6:
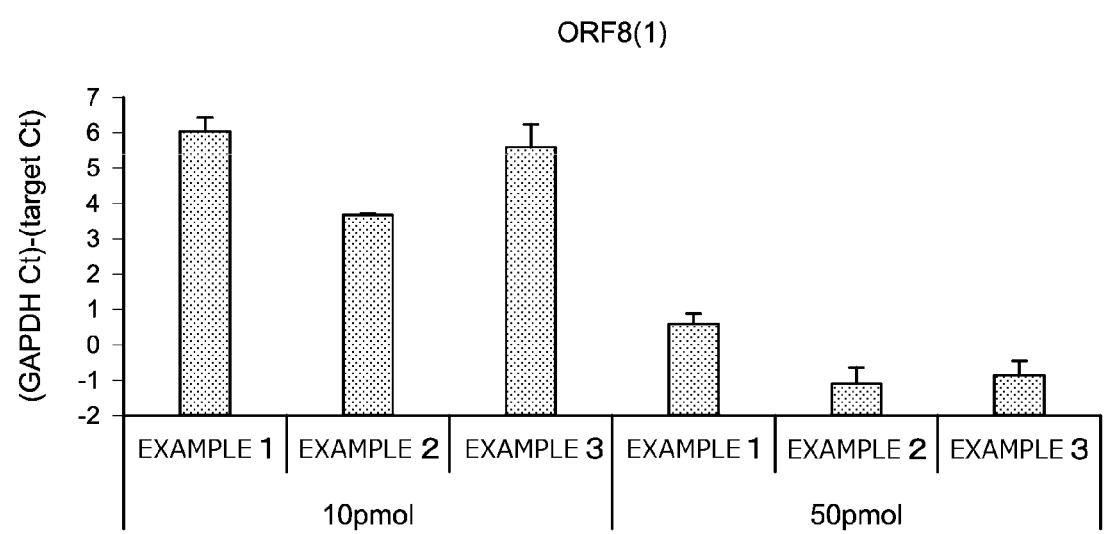
FIG. 6 is a graph showing changes in the amount of RNA of ORF8 (1) contained in SARS-CoV-2-infected cell-extracted samples through transfection with siRNA shown in Examples 1 to 3.
Figure 7:
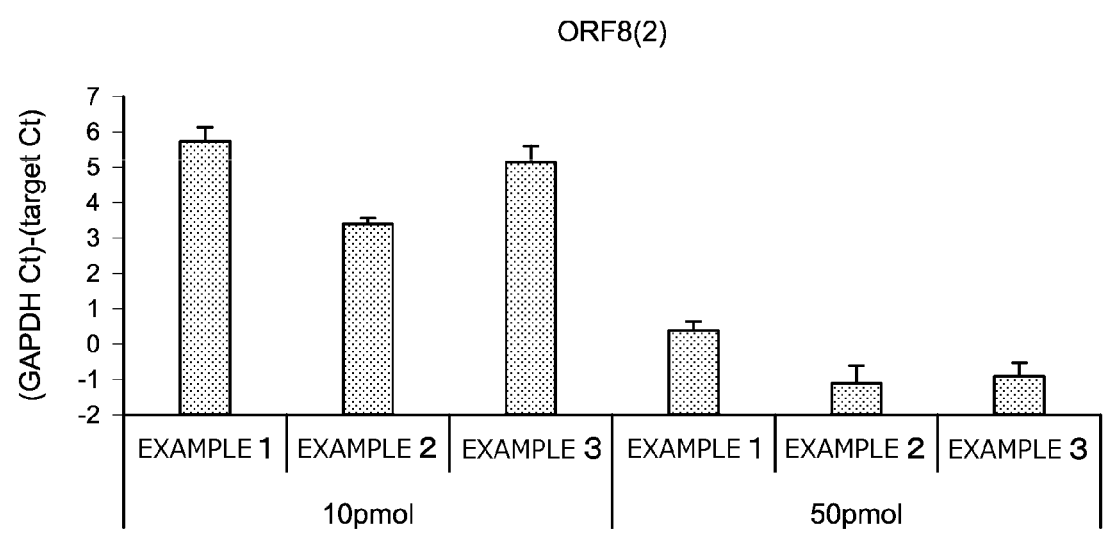
FIG. 7 is a graph showing changes in the amount of RNA of ORF8 (2) contained in SARS-CoV-2-infected cell-extracted samples through transfection with siRNA shown in Examples 1 to 3.

Next, in order to compare the proliferation numbers of SARS-CoV-2, the amounts of RNA of SARS-CoV-2 contained in the above-prepared supernatant samples of Reference Example 1 and Examples 1 to 3 were measured through quantitative PCR (qPCR). StepOnePlus (trademark) Real-Time PCR System (manufactured by Thermo Fisher Scientific Inc.) was used as a PCR machine. A primer targeting N-sarbeco was used as a primer. Primer sequences are shown in Table 2. The primer of N-sarbeco targets a region of conserving N proteins possessed by the genus Sarbecovirus (a genus name to which SARS-CoV-2 belongs). Here, the amount of RNA of N-sarbeco obtained through qPCR is shown as the number of RNA copies of SARS-CoV-2 (number of viral RNA copies). In qPCR of the supernatant samples, One Step TB Green PrimeScript PLUS RT-PCR Kit (Perfect Real Time) (manufactured by Takara Bio Inc.) was used as a qPCR reagent, and the same PCR machine as described above was used. The results are shown in FIG. 3. A standard curve was created using RNA ($10^5$ copies/μL) of SARS-CoV-2 purchased from Nihon Gene Research Laboratories Inc.

TABLE 2

| Origin | Amplification region | Primer sequence |
|---|---|---|
| SARS-CoV-2 | S protein | Forward: cttccctcagtcagcac ctc (SEQ ID NO: 19)<br>Reverse: aaccagtgtgtgccatt tga (SEQ ID NO: 20) |
| | ORF 8 (1) | Forward: gctgcatttcaccaaga atg (SEQ ID NO: 21)<br>Reverse: ctcatccacgcacaatt caa (SEQ ID NO: 22) |
| | ORF 8 (2) | Forward: cactttgcttcacactc aaaaga (SEQ ID NO: 23)<br>Reverse: cattcttggtgaaatgc agcta (SEQ ID NO: 24) |
| | SARS-CoV-2-N | Forward: ccaggtaacaaaccaac caactttcg (SEQ ID NO: 25)<br>Reverse: ggttactgccagttgaa tctgagg (SEQ ID NO: 26) |
| | N-sarbeco | Forward: agcctcttctcgttcct catcac (SEQ ID NO: 27)<br>Reverse: ccgccattgccagccat tc (SEQ ID NO: 28) |
| Human | GAPDH | Forward: ggagcgagatccctcca aaat (SEQ ID NO: 29)<br>Reverse: ggctgttgtcatacttc tcatgg (SEQ ID NO: 30) |

FIG. 3 is a graph showing the number of RNA copies of SARS-CoV-2 contained in the supernatant samples. Here, the number of RNA copies was corrected so as to be a value per 1,000 ng of the total amount of RNA obtained from the cells. That is, the values shown in FIG. 3 can be regarded as amounts of viral RNA produced per unit cell. As shown in FIG. 3, in Examples 1 to 3, it was confirmed that the number of viral RNA copies per unit cell can be significantly reduced by increasing the amount of siRNA added.

Next, the amount of RNA of SARS-CoV-2 in the cell extraction samples was quantitatively determined through qPCR. SYBR Green real-time PCR Master Mix (manufactured by Thermo Fisher Scientific Inc.) was used as a reagent for qPCR, and the same PCR machine as that described above was used. Four types of primers targeting an internal region of an S protein, an internal region (denoted as "ORF8 (1)") of ORF8, a region from upstream of ORF8 to the inside of ORF8 (denoted as "ORF8 (2)"), and a region specific to SARS-CoV-2 of an N protein (denoted as "SARS-CoV-2-N") were used (refer to Table 2). In addition, qPCR targeting human GAPDH for standardizing qPCR was performed (refer to Table 2 for primers).

FIGS. 4 to 7 show values obtained by subtracting Ct values of various target regions in supernatant samples from Ct values of GAPDH of cell extraction samples. FIGS. 4 to 7 show that the smaller the value on the longitudinal axis, the smaller the abundance of RNA of SARS-CoV-2.

As shown in FIGS. 4 to 7, it can be seen that Examples 1 to 3 reduced the abundance of RNA in other regions as well as in the S protein targeting siRNA. That is, in Examples 1 to 3, it can be seen that the proliferation of SARS-CoV-2 (increase in genomic RNA) was suppressed. In addition, in all of Examples 1 to 3, it was confirmed that the proliferation of RNA of SARS-CoV-2 can be more effectively suppressed when 50 pmol of siRNA was added.

Test 2

Next, the siRNA of Example 2 was used to further examine an siRNA concentration-dependent effect of suppressing proliferation of SARS-CoV-2. The method of Test 1 described above was performed similarly except that the concentration of siRNA in a medium during transfection was set to 0 nM (that is, only a transfection reagent), 6.25 nM, 12.5 nM, 25 nM, and 50 nM. In addition, an example infected with SARS-CoV-2 without adding siRNA and a transfection reagent was performed as Reference Example 2.

Figure 8:
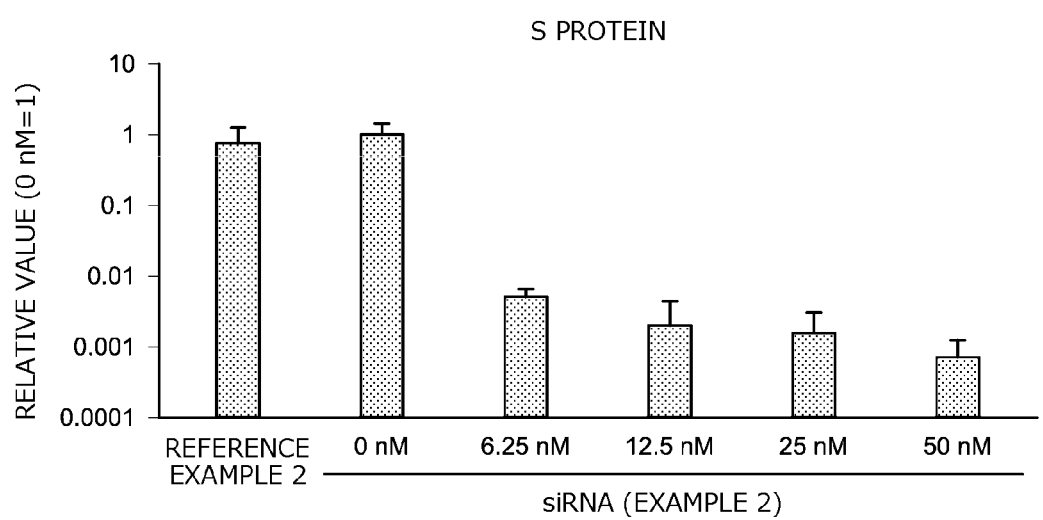
FIG. 8 is a graph showing changes in the amount of RNA of S protein contained in a SARS-CoV-2-infected cell-extracted sample when siRNA shown in Example 2 is transfected in a concentration range of 0 to 50 nM.
Figure 9:
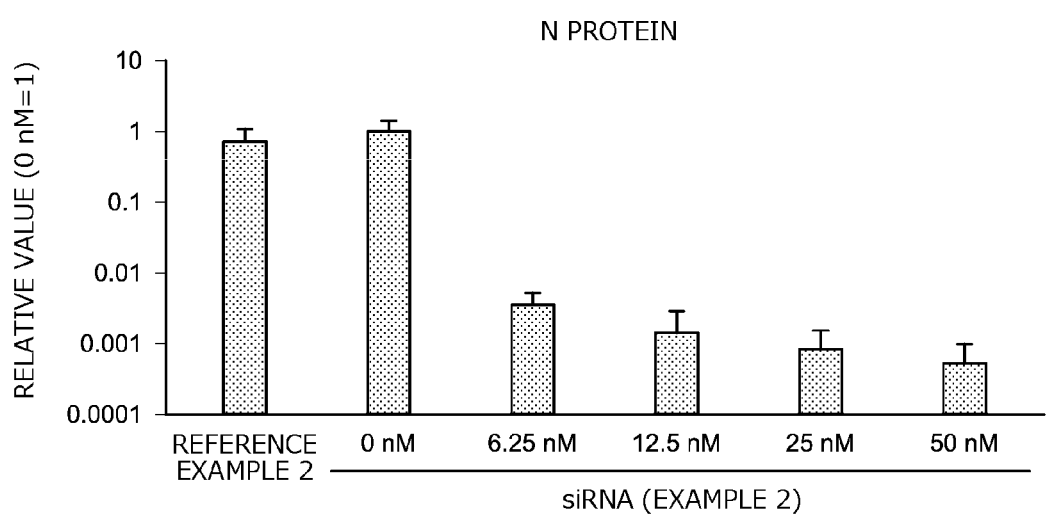
FIG. 9 is a graph showing changes in the amount of RNA of N protein contained in a SARS-CoV-2-infected cell-extracted sample when siRNA shown in Example 2 is transfected in a concentration range of 0 to 50 nM.

In Test 2, the amounts of RNA of the S protein and the N protein contained in cell extraction samples were quantitatively determined through qPCR, respectively. The method of qPCR performed was the same as that of qPCR of the cell samples in Test 1, and primers targeting the S protein and SARS-CoV-2-N shown in Table 2 were used as primers. The results are shown in FIGS. 8 and 9. FIGS. 8 and 9 show relative values when a case where 0 nM of siRNA is added is set to 1.

As shown in FIGS. 8 and 9, it can be seen that the amounts of RNA of SARS-CoV-2 in the cell extraction samples were reduced depending on the concentration of siRNA by transfecting the siRNA used in Example 2. Furthermore, even when the concentration of the siRNA was set to 6.25 nM, the amounts of RNA of the S protein and the N protein were 1/100 or less compared to the case of 0 nM. Accordingly, it can be seen that the siRNA used in Example 2 can significantly suppress the proliferation of SARS-CoV-2 even at a low concentration.

Test 3

Eurofins Genomics K.K. was asked to synthesize polynucleotides, and 8 kinds of polynucleotides were obtained in Test 3. Base sequences of the polynucleotides are shown in Table 3. In each polynucleotide, "TT" (overhang) on the 3' terminal side is DNA, and the other portion of the sequence (target sequence) is composed of RNA. The obtained polynucleotides were used to prepare siRNAs used in Examples 7 to 10 by annealing sense strands and antisense strands having complementary sequences. Examples 7 to 10 shown in Table 3 are siRNAs designed to contain at least a part of a base sequence encoding a signal peptide region of an S protein of the SARS-CoV-2.

TABLE 3

Configuration of siRNA

| Example 7 | Sense strand:<br>Antisense strand: | 5'<br>3' | GUUUGUUUUCUUGUUUUAUU<br>TTCAAACAAAAGAACAAAAU | 3'<br>5' | (SEQ ID NO: 35)<br>(SEQ ID NO: 36) |
|---|---|---|---|---|---|
| Example 8 | Sense strand:<br>Antisense strand: | 5'<br>3' | CCACUAGUCUCUAGUCAGUTT<br>TTGGUGAUCAGAGAUCAGUCA | 3'<br>5' | (SEQ ID NO: 37)<br>(SEQ ID NO: 38) |
| Example 9 | Sense strand:<br>Antisense strand: | 5'<br>3' | CUCUAGUCAGUGUGUUAAUTT<br>TTGAGAUCAGUCACACAAUUA | 3'<br>5' | (SEQ ID NO: 39)<br>(SEQ ID NO: 40) |
| Example 10 | Sense strand:<br>Antisense strand: | 5'<br>3' | CUAGUCAGUGUGUUAAUCUTT<br>TTGAUCAGUCACACAAUUAGA | 3'<br>5' | (SEQ ID NO: 41)<br>(SEQ ID NO: 42) |

Examples 7 to 10

Supernatant samples and cell extraction samples were prepared in the same manner as in Test 1 except that siRNAs used were changed to the siRNAs shown in Table 3. In addition, a system in which no siRNA was added (that is, siRNA was 0 nM) was simultaneously carried out. qPCR in which the primer targeting N-sarbeco shown in Table 2 was used was performed on the supernatant samples, and the number of RNA copies of SARS-CoV-2 per 1 mL of each of the supernatant samples was measured. The method of qPCR performed is the same as that of qPCR of the supernatant samples in Test 1. The results are shown in FIG. 10.

Figure 10:
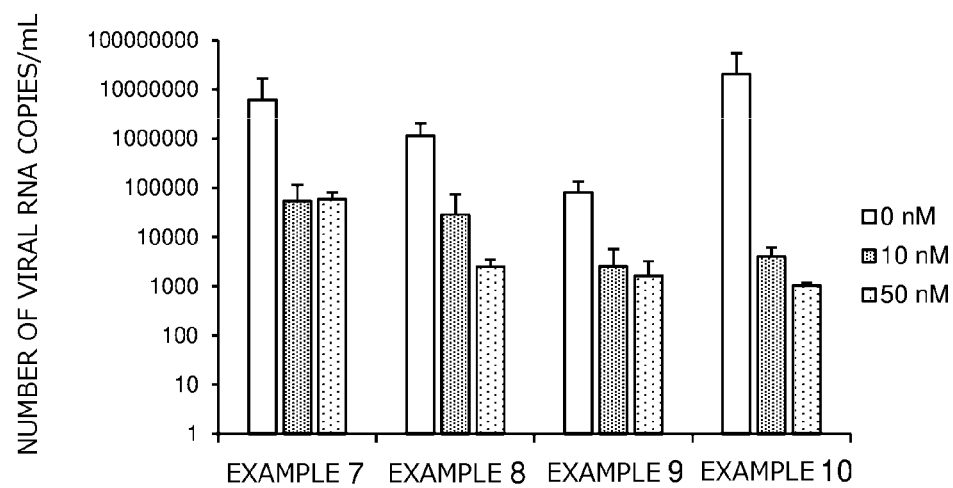
FIG. 10 is a graph showing the number of RNA copies of SARS-CoV-2 viruses contained in 1 mL of a culture medium (supernatant sample) after infection with SARS-CoV-2 and transfection with siRNA shown in Examples 7 to 10.

As shown in FIG. 10, it can be seen that, in all of Examples 7 to 10, the number of RNA copies of SARS-CoV-2 contained in the supernatant samples is reduced by adding siRNA. In particular, it can be seen that, in Examples 8 to 10, the number of RNA copies of SARS-CoV-2 contained in the supernatant samples was reduced depending on the concentration of siRNA.

Figure 11:
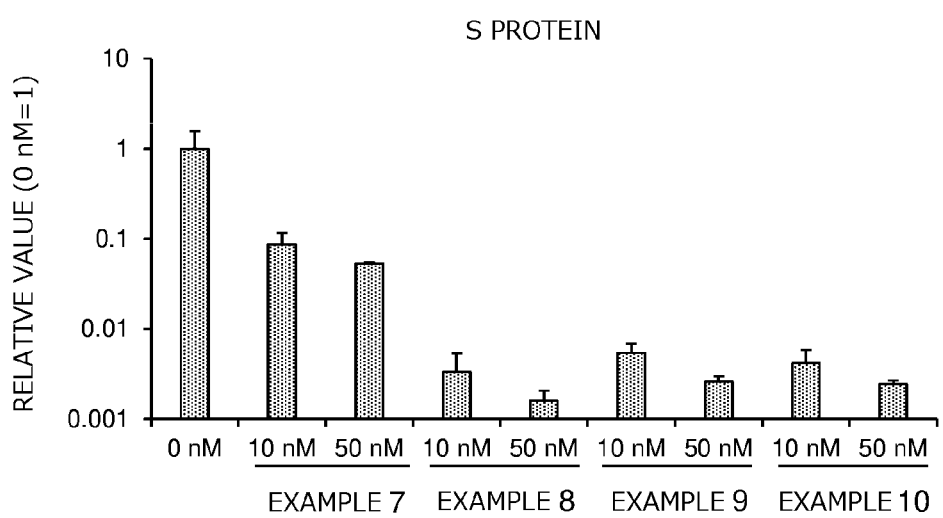
FIG. 11 is a graph showing changes in the amount of RNA of S protein contained in SARS-CoV-2-infected cell-extracted samples when siRNA shown in Examples 7 to 10 are transfected at a concentration of 10 nM or 50 nM.
Figure 12:
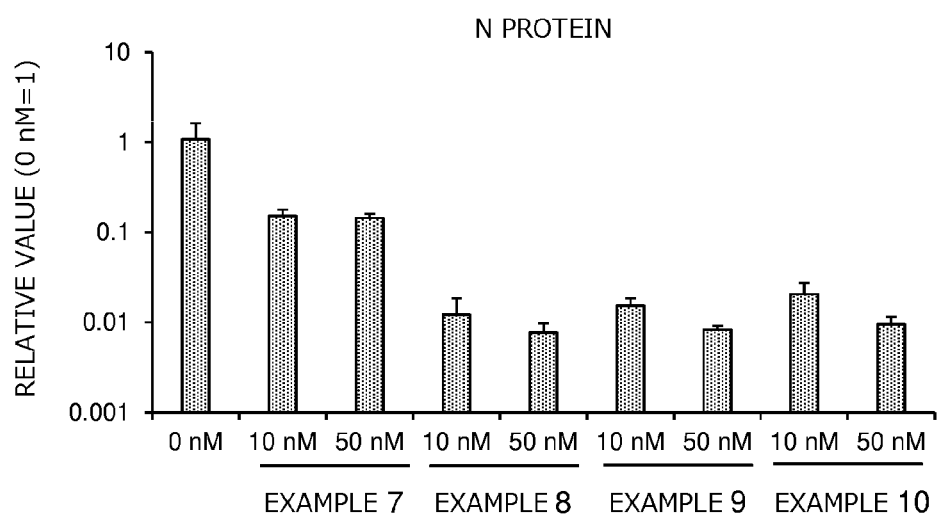
FIG. 12 is a graph showing changes in the amount of RNA of N protein contained in SARS-CoV-2-infected cell-extracted samples when siRNA shown in Examples 7 to 10 are transfected at a concentration of 10 nM or 50 nM.

In addition, the amounts of RNA of an S protein and an N protein contained in cell extraction samples were quantitatively determined through qPCR, respectively. The method of qPCR performed was the same as that of qPCR of the cell samples in Test 1, and primers targeting the S protein and SARS-CoV-2-N shown in Table 2 were used as primers. The results are shown in FIGS. 11 and 12. FIGS. 11 and 12 show relative values when a case where 0 nM of siRNA is added (that is, not added) is set to 1.

As shown in FIGS. 11 and 12, it can be seen that, in all of Examples 7 to 10, the amounts of RNA of the S protein and the N protein in the cell extraction samples are reduced by adding siRNA. That is, it can be seen that the siRNAs used in Examples 7 to 10 suppress the proliferation of SARS-CoV-2. In addition, it can be seen that, in the siRNAs used in Examples 8 to 10, the amounts of RNA of the S protein and the N protein in the cell extraction samples can be reduced depending on the concentration of siRNA. Furthermore, it was confirmed that even if the concentration of the siRNAs used in Examples 8 to 10 is as low as 10 nM, the amounts of RNA of the S protein and the N protein can be set to 1/100 or less compared to the case of 0 nM. Accordingly, it can be seen that the siRNAs used in Examples 8 to 10 can significantly suppress the proliferation of SARS-CoV-2.

Although not particularly limited, from the test examples, the mechanism of suppressing the proliferation of SARS-CoV-2 due to the siRNA disclosed herein is estimated as follows. Since the siRNA disclosed herein targets at least a part of a signal peptide region of an S protein, a target sequence of genomic RNA of SARS-CoV-2 decomposes or is inhibited from being translated. Accordingly, expression of the S protein is suppressed. For this reason, the amount of the S protein on SARS-CoV-2 particles is reduced, and the frequency of the S protein binding to ACE2 present on the surface of human cells is reduced. As a result, the spread of infection with SARS-CoV-2 particles can be suppressed, and the proliferation of SARS-CoV-2 can be suppressed. On the other hand, it is estimated from Examples 4 to 6 in which no effect of suppressing proliferation of SARS-CoV-2 was obtained that the ORF8 protein was not indispensable for the mechanism of the spread of infection with SARS-CoV-2. That is, it can be stated that the effect of suppressing proliferation of SARS-CoV-2 due to siRNA can depend on its target sequence and the siRNA disclosed herein can significantly suppress the proliferation of SARS-CoV-2.

Specific examples of the technology disclosed herein are shown in detail in the preceding, but these are nothing more than examples and do not limit the scope of the claims. Various and diverse modifications and alterations to the specific examples provided above as examples are included in the art described in the claims.

The siRNA disclosed herein can exhibit a significant effect of suppressing proliferation of SARS-CoV-2 and increase the number of living cells. For this reason, the siRNA disclosed herein can be used as a therapeutic agent for SARS-CoV-2. In addition, since the siRNA disclosed herein targets at least a part of a signal peptide region of an S protein of SARS-CoV-2 which is presumed to be unlikely to cause an amino acid mutation, the proliferation-suppressing effect can also be exhibited on SARS-CoV-2 mutant strains.

What is claimed is:
1. SiRNA comprising:
a sense strand; and
an antisense strand,
wherein the sense strand includes
a target sequence comprising 19 to 23 bases in which a base at a 5' terminal is guanine (G) or cytosine (C), and
an overhang comprising 2 to 4 bases added to a 3' terminal side of the target sequence,
wherein the antisense strand includes
a sequence complementary to the target sequence, and
an overhang comprising 2 to 4 bases added to a 3' terminal side of the complementary sequence, and
the target sequence includes (1) or (2) below:

```
(1)
                              (SEQ ID NO: 1)
GUUUUAUUGCCACUAGUCU;

(2)
                              (SEQ ID NO: 31)
GUUUGUUUUCUUGUUUUA;
```

2. The siRNA according to claim 1,
wherein base sequences constituting the overhangs are thymine-thymine (TT).
3. A composition for suppressing proliferation of SARS-COV-2, the composition comprising:
the siRNA according to claim 1.

\* \* \* \* \*

SEQUENCE LISTING

```
Sequence total quantity: 42
SEQ ID NO: 1            moltype = RNA   length = 19
FEATURE                 Location/Qualifiers
misc_feature            1..19
                        note = target sequence in siRNA
source                  1..19
                        mol_type = other RNA
```

```
                        organism = synthetic construct
SEQUENCE: 1
gttttattgc cactagtct                                            19

SEQ ID NO: 2            moltype = RNA   length = 19
FEATURE                 Location/Qualifiers
misc_feature            1..19
                        note = target sequence in siRNA
source                  1..19
                        mol_type = other RNA
                        organism = synthetic construct
SEQUENCE: 2
gtctctagtc agtgtgtta                                            19

SEQ ID NO: 3            moltype = RNA   length = 19
FEATURE                 Location/Qualifiers
misc_feature            1..19
                        note = target sequence in siRNA
source                  1..19
                        mol_type = other RNA
                        organism = synthetic construct
SEQUENCE: 3
cagtgtgtta atcttacaa                                            19

SEQ ID NO: 4            moltype = AA   length = 16
FEATURE                 Location/Qualifiers
source                  1..16
                        mol_type = protein
                        organism = Severe acute respiratory syndrome coronavirus 2
SEQUENCE: 4
MFVFLVLLPL VSSQCV                                               16

SEQ ID NO: 5            moltype = RNA   length = 48
FEATURE                 Location/Qualifiers
source                  1..48
                        mol_type = viral cRNA
                        organism = Severe acute respiratory syndrome coronavirus 2
SEQUENCE: 5
atgtttgttt ttcttgtttt attgccacta gtctctagtc agtgtgtt            48

SEQ ID NO: 6            moltype = DNA   length = 21
FEATURE                 Location/Qualifiers
misc_feature            1..19
                        note = RNA
source                  1..21
                        mol_type = other DNA
                        organism = synthetic construct
modified_base           2..5
                        mod_base = OTHER
                        note = uracil
modified_base           7..8
                        mod_base = OTHER
                        note = uracil
modified_base           14
                        mod_base = OTHER
                        note = uracil
modified_base           17
                        mod_base = OTHER
                        note = uracil
modified_base           19
                        mod_base = OTHER
                        note = uracil
misc_feature            20..21
                        note = DNA
SEQUENCE: 6
gttttattgc cactagtctt t                                         21

SEQ ID NO: 7            moltype = DNA   length = 21
FEATURE                 Location/Qualifiers
misc_feature            1..19
                        note = RNA
source                  1..21
                        mol_type = other DNA
                        organism = synthetic construct
modified_base           5
                        mod_base = OTHER
                        note = uracil
modified_base           8
                        mod_base = OTHER
```

```
                         note = uracil
modified_base            14
                         mod_base = OTHER
                         note = uracil
misc_feature             20..21
                         note = DNA
SEQUENCE: 7
agactagtgg caataaaact t                                               21

SEQ ID NO: 8             moltype = DNA   length = 21
FEATURE                  Location/Qualifiers
misc_feature             1..19
                         note = RNA
source                   1..21
                         mol_type = other DNA
                         organism = synthetic construct
modified_base            2
                         mod_base = OTHER
                         note = uracil
modified_base            4
                         mod_base = OTHER
                         note = uracil
modified_base            6
                         mod_base = OTHER
                         note = uracil
modified_base            9
                         mod_base = OTHER
                         note = uracil
modified_base            13
                         mod_base = OTHER
                         note = uracil
modified_base            15
                         mod_base = OTHER
                         note = uracil
modified_base            17..18
                         mod_base = OTHER
                         note = uracil
misc_feature             20..21
                         note = DNA
SEQUENCE: 8
gtctctagtc agtgtgttat t                                               21

SEQ ID NO: 9             moltype = DNA   length = 21
FEATURE                  Location/Qualifiers
misc_feature             1..19
                         note = RNA
source                   1..21
                         mol_type = other DNA
                         organism = synthetic construct
modified_base            1
                         mod_base = OTHER
                         note = uracil
modified_base            9
                         mod_base = OTHER
                         note = uracil
modified_base            13
                         mod_base = OTHER
                         note = uracil
misc_feature             20..21
                         note = DNA
SEQUENCE: 9
taacacactg actagagact t                                               21

SEQ ID NO: 10            moltype = DNA   length = 21
FEATURE                  Location/Qualifiers
misc_feature             1..19
                         note = RNA
source                   1..21
                         mol_type = other DNA
                         organism = synthetic construct
modified_base            4
                         mod_base = OTHER
                         note = uracil
modified_base            6
                         mod_base = OTHER
                         note = uracil
modified_base            8..9
                         mod_base = OTHER
                         note = uracil
```

```
modified_base               12
                            mod_base = OTHER
                            note = uracil
modified_base               14..15
                            mod_base = OTHER
                            note = uracil
misc_feature                20..21
                            note = DNA
SEQUENCE: 10
cagtgtgtta atcttacaat t                                              21

SEQ ID NO: 11               moltype = DNA   length = 21
FEATURE                     Location/Qualifiers
misc_feature                1..19
                            note = RNA
source                      1..21
                            mol_type = other DNA
                            organism = synthetic construct
modified_base               1..2
                            mod_base = OTHER
                            note = uracil
modified_base               4
                            mod_base = OTHER
                            note = uracil
modified_base               9..10
                            mod_base = OTHER
                            note = uracil
modified_base               18
                            mod_base = OTHER
                            note = uracil
misc_feature                20..21
                            note = DNA
SEQUENCE: 11
ttgtaagatt aacacactgt t                                              21

SEQ ID NO: 12               moltype = DNA   length = 21
FEATURE                     Location/Qualifiers
misc_feature                1..19
                            note = RNA
source                      1..21
                            mol_type = other DNA
                            organism = synthetic construct
modified_base               2..5
                            mod_base = OTHER
                            note = uracil
modified_base               7..8
                            mod_base = OTHER
                            note = uracil
modified_base               14
                            mod_base = OTHER
                            note = uracil
modified_base               17
                            mod_base = OTHER
                            note = uracil
misc_feature                20..21
                            note = DNA
SEQUENCE: 12
gttttcttag gaatcatcat t                                              21

SEQ ID NO: 13               moltype = DNA   length = 21
FEATURE                     Location/Qualifiers
misc_feature                1..19
                            note = RNA
source                      1..21
                            mol_type = other DNA
                            organism = synthetic construct
modified_base               1
                            mod_base = OTHER
                            note = uracil
modified_base               4
                            mod_base = OTHER
                            note = uracil
modified_base               7..8
                            mod_base = OTHER
                            note = uracil
modified_base               11
                            mod_base = OTHER
                            note = uracil
misc_feature                20..21
```

-continued

```
                          note = DNA
SEQUENCE: 13
tgatgattcc taagaaaact t                                              21

SEQ ID NO: 14             moltype = DNA   length = 21
FEATURE                   Location/Qualifiers
misc_feature              1..19
                          note = RNA
source                    1..21
                          mol_type = other DNA
                          organism = synthetic construct
modified_base             3
                          mod_base = OTHER
                          note = uracil
modified_base             7..9
                          mod_base = OTHER
                          note = uracil
modified_base             19
                          mod_base = OTHER
                          note = uracil
misc_feature              20..21
                          note = DNA
SEQUENCE: 14
gctgcatttc accaagaatt t                                              21

SEQ ID NO: 15             moltype = DNA   length = 21
FEATURE                   Location/Qualifiers
misc_feature              1..19
                          note = RNA
source                    1..21
                          mol_type = other DNA
                          organism = synthetic construct
modified_base             2..3
                          mod_base = OTHER
                          note = uracil
modified_base             5..6
                          mod_base = OTHER
                          note = uracil
modified_base             9
                          mod_base = OTHER
                          note = uracil
modified_base             14
                          mod_base = OTHER
                          note = uracil
misc_feature              20..21
                          note = DNA
SEQUENCE: 15
attcttggtg aaatgcagct t                                              21

SEQ ID NO: 16             moltype = DNA   length = 21
FEATURE                   Location/Qualifiers
misc_feature              1..19
                          note = RNA
source                    1..21
                          mol_type = other DNA
                          organism = synthetic construct
modified_base             7
                          mod_base = OTHER
                          note = uracil
modified_base             9
                          mod_base = OTHER
                          note = uracil
modified_base             12..14
                          mod_base = OTHER
                          note = uracil
modified_base             19
                          mod_base = OTHER
                          note = uracil
misc_feature              20..21
                          note = DNA
SEQUENCE: 16
caagaatgta gtttacagtt t                                              21

SEQ ID NO: 17             moltype = DNA   length = 21
FEATURE                   Location/Qualifiers
misc_feature              1..19
                          note = RNA
source                    1..21
                          mol_type = other DNA
```

-continued

```
                     organism = synthetic construct
modified_base        3
                     mod_base = OTHER
                     note = uracil
modified_base        5
                     mod_base = OTHER
                     note = uracil
modified_base        10
                     mod_base = OTHER
                     note = uracil
modified_base        14..15
                     mod_base = OTHER
                     note = uracil
modified_base        17..18
                     mod_base = OTHER
                     note = uracil
misc_feature         20..21
                     note = DNA
SEQUENCE: 17
actgtaaact acattcttgt t                                            21

SEQ ID NO: 18        moltype = RNA  length = 45
FEATURE              Location/Qualifiers
source               1..45
                     mol_type = viral cRNA
                     organism = Severe acute respiratory syndrome coronavirus 2
SEQUENCE: 18
atgaaatttc ttgttttctt aggaatcatc acaactgtag ctgca                  45

SEQ ID NO: 19        moltype = DNA  length = 20
FEATURE              Location/Qualifiers
misc_feature         1..20
                     note = PCR_primers_fwd_seq
source               1..20
                     mol_type = other DNA
                     organism = synthetic construct
SEQUENCE: 19
cttccctcag tcagcacctc                                              20

SEQ ID NO: 20        moltype = DNA  length = 20
FEATURE              Location/Qualifiers
misc_feature         1..20
                     note = PCR_primers_rev_seq
source               1..20
                     mol_type = other DNA
                     organism = synthetic construct
SEQUENCE: 20
aaccagtgtg tgccatttga                                              20

SEQ ID NO: 21        moltype = DNA  length = 20
FEATURE              Location/Qualifiers
misc_feature         1..20
                     note = PCR_primers_fwd_seq
source               1..20
                     mol_type = other DNA
                     organism = synthetic construct
SEQUENCE: 21
gctgcatttc accaagaatg                                              20

SEQ ID NO: 22        moltype = DNA  length = 20
FEATURE              Location/Qualifiers
misc_feature         1..20
                     note = PCR_primers_rev_seq
source               1..20
                     mol_type = other DNA
                     organism = synthetic construct
SEQUENCE: 22
ctcatccacg cacaattcaa                                              20

SEQ ID NO: 23        moltype = DNA  length = 23
FEATURE              Location/Qualifiers
misc_feature         1..23
                     note = PCR_primers_fwd_seq
source               1..23
                     mol_type = other DNA
                     organism = synthetic construct
SEQUENCE: 23
cactttgctt cacactcaaa aga                                          23
```

```
SEQ ID NO: 24              moltype = DNA   length = 22
FEATURE                    Location/Qualifiers
misc_feature               1..22
                           note = PCR_primers_rev_seq
source                     1..22
                           mol_type = other DNA
                           organism = synthetic construct
SEQUENCE: 24
cattcttggt gaaatgcagc ta                                              22

SEQ ID NO: 25              moltype = DNA   length = 26
FEATURE                    Location/Qualifiers
misc_feature               1..26
                           note = PCR_primers_fwd_seq
source                     1..26
                           mol_type = other DNA
                           organism = synthetic construct
SEQUENCE: 25
ccaggtaaca aaccaaccaa ctttcg                                          26

SEQ ID NO: 26              moltype = DNA   length = 24
FEATURE                    Location/Qualifiers
misc_feature               1..24
                           note = PCR_primers_rev_seq
source                     1..24
                           mol_type = other DNA
                           organism = synthetic construct
SEQUENCE: 26
ggttactgcc agttgaatct gagg                                            24

SEQ ID NO: 27              moltype = DNA   length = 23
FEATURE                    Location/Qualifiers
misc_feature               1..23
                           note = PCR_primers_fwd_seq
source                     1..23
                           mol_type = other DNA
                           organism = synthetic construct
SEQUENCE: 27
agcctcttct cgttcctcat cac                                             23

SEQ ID NO: 28              moltype = DNA   length = 19
FEATURE                    Location/Qualifiers
misc_feature               1..19
                           note = PCR_primers_rev_seq
source                     1..19
                           mol_type = other DNA
                           organism = synthetic construct
SEQUENCE: 28
ccgccattgc cagccattc                                                  19

SEQ ID NO: 29              moltype = DNA   length = 21
FEATURE                    Location/Qualifiers
misc_feature               1..21
                           note = PCR_primers_fwd_seq
source                     1..21
                           mol_type = other DNA
                           organism = synthetic construct
SEQUENCE: 29
ggagcgagat ccctccaaaa t                                               21

SEQ ID NO: 30              moltype = DNA   length = 23
FEATURE                    Location/Qualifiers
misc_feature               1..23
                           note = PCR_primers_rev_seq
source                     1..23
                           mol_type = other DNA
                           organism = synthetic construct
SEQUENCE: 30
ggctgttgtc atacttctca tgg                                             23

SEQ ID NO: 31              moltype = RNA   length = 19
FEATURE                    Location/Qualifiers
misc_feature               1..19
                           note = target sequence in siRNA
source                     1..19
                           mol_type = other RNA
                           organism = synthetic construct
SEQUENCE: 31
gtttgttttt cttgttttta                                                 19
```

```
SEQ ID NO: 32              moltype = RNA   length = 19
FEATURE                    Location/Qualifiers
misc_feature               1..19
                           note = target sequence in siRNA
source                     1..19
                           mol_type = other RNA
                           organism = synthetic construct
SEQUENCE: 32
ccactagtct ctagtcagt                                                       19

SEQ ID NO: 33              moltype = RNA   length = 19
FEATURE                    Location/Qualifiers
misc_feature               1..19
                           note = target sequence in siRNA
source                     1..19
                           mol_type = other RNA
                           organism = synthetic construct
SEQUENCE: 33
ctctagtcag tgtgttaat                                                       19

SEQ ID NO: 34              moltype = RNA   length = 19
FEATURE                    Location/Qualifiers
misc_feature               1..19
                           note = target sequence in siRNA
source                     1..19
                           mol_type = other RNA
                           organism = synthetic construct
SEQUENCE: 34
ctagtcagtg tgttaatct                                                       19

SEQ ID NO: 35              moltype = DNA   length = 21
FEATURE                    Location/Qualifiers
misc_feature               1..19
                           note = RNA
source                     1..21
                           mol_type = other DNA
                           organism = synthetic construct
modified_base              2..4
                           mod_base = OTHER
                           note = uracil
modified_base              6..10
                           mod_base = OTHER
                           note = uracil
modified_base              12..13
                           mod_base = OTHER
                           note = uracil
modified_base              15..18
                           mod_base = OTHER
                           note = uracil
misc_feature               20..21
                           note = DNA
SEQUENCE: 35
gtttgttttt cttgttttat t                                                    21

SEQ ID NO: 36              moltype = DNA   length = 21
FEATURE                    Location/Qualifiers
misc_feature               1..19
                           note = RNA
source                     1..21
                           mol_type = other DNA
                           organism = synthetic construct
modified_base              1
                           mod_base = OTHER
                           note = uracil
misc_feature               20..21
                           note = DNA
SEQUENCE: 36
taaaacaaga aaacaaact t                                                     21

SEQ ID NO: 37              moltype = DNA   length = 21
FEATURE                    Location/Qualifiers
misc_feature               1..19
                           note = RNA
source                     1..21
                           mol_type = other DNA
                           organism = synthetic construct
modified_base              5
                           mod_base = OTHER
```

```
                            note       = uracil
modified_base               8
                            mod_base   = OTHER
                            note       = uracil
modified_base               10
                            mod_base   = OTHER
                            note       = uracil
modified_base               12
                            mod_base   = OTHER
                            note       = uracil
modified_base               15
                            mod_base   = OTHER
                            note       = uracil
modified_base               19
                            mod_base   = OTHER
                            note       = uracil
misc_feature                20..21
                            note       = DNA
SEQUENCE: 37
ccactagtct ctagtcagtt t                                              21

SEQ ID NO: 38               moltype = DNA   length = 21
FEATURE                     Location/Qualifiers
misc_feature                1..19
                            note       = RNA
source                      1..21
                            mol_type   = other DNA
                            organism   = synthetic construct
modified_base               3
                            mod_base   = OTHER
                            note       = uracil
modified_base               7
                            mod_base   = OTHER
                            note       = uracil
modified_base               14
                            mod_base   = OTHER
                            note       = uracil
modified_base               17
                            mod_base   = OTHER
                            note       = uracil
misc_feature                20..21
                            note       = DNA
SEQUENCE: 38
actgactaga gactagtggt t                                              21

SEQ ID NO: 39               moltype = DNA   length = 21
FEATURE                     Location/Qualifiers
misc_feature                1..19
                            note       = RNA
source                      1..21
                            mol_type   = other DNA
                            organism   = synthetic construct
modified_base               2
                            mod_base   = OTHER
                            note       = uracil
modified_base               4
                            mod_base   = OTHER
                            note       = uracil
modified_base               7
                            mod_base   = OTHER
                            note       = uracil
modified_base               11
                            mod_base   = OTHER
                            note       = uracil
modified_base               13
                            mod_base   = OTHER
                            note       = uracil
modified_base               15..16
                            mod_base   = OTHER
                            note       = uracil
modified_base               19
                            mod_base   = OTHER
                            note       = uracil
misc_feature                20..21
                            note       = DNA
SEQUENCE: 39
ctctagtcag tgtgttaatt t                                              21

SEQ ID NO: 40               moltype = DNA   length = 21
```

```
FEATURE                 Location/Qualifiers
misc_feature            1..19
                        note = RNA
source                  1..21
                        mol_type = other DNA
                        organism = synthetic construct
modified_base           2..3
                        mod_base = OTHER
                        note = uracil
modified_base           11
                        mod_base = OTHER
                        note = uracil
modified_base           15
                        mod_base = OTHER
                        note = uracil
misc_feature            20..21
                        note = DNA
SEQUENCE: 40
attaacacac tgactagagt t                                              21

SEQ ID NO: 41           moltype = DNA  length = 21
FEATURE                 Location/Qualifiers
misc_feature            1..19
                        note = RNA
source                  1..21
                        mol_type = other DNA
                        organism = synthetic construct
modified_base           2
                        mod_base = OTHER
                        note = uracil
modified_base           5
                        mod_base = OTHER
                        note = uracil
modified_base           9
                        mod_base = OTHER
                        note = uracil
modified_base           11
                        mod_base = OTHER
                        note = uracil
modified_base           13..14
                        mod_base = OTHER
                        note = uracil
modified_base           17
                        mod_base = OTHER
                        note = uracil
modified_base           19
                        mod_base = OTHER
                        note = uracil
misc_feature            20..21
                        note = DNA
SEQUENCE: 41
ctagtcagtg tgttaatctt t                                              21

SEQ ID NO: 42           moltype = DNA  length = 21
FEATURE                 Location/Qualifiers
misc_feature            1..19
                        note = RNA
source                  1..21
                        mol_type = other DNA
                        organism = synthetic construct
modified_base           4..5
                        mod_base = OTHER
                        note = uracil
modified_base           13
                        mod_base = OTHER
                        note = uracil
modified_base           17
                        mod_base = OTHER
                        note = uracil
misc_feature            20..21
                        note = DNA
SEQUENCE: 42
agattaacac actgactagt t                                              21
```